United States Patent [19]

Katsube et al.

[11] 4,241,070
[45] Dec. 23, 1980

[54] ANALGESIC BENZOMORPHAN DERIVATIVES

[75] Inventors: Junki Katsube, Toyonaka; Hiroyuki Mizote; Shuichi Harada, both of Ibaragi; Hisao Yamamoto, Kobe, all of Japan

[73] Assignee: Sumitomo Chemical Company, Limited, Osaka, Japan

[21] Appl. No.: 736,072

[22] Filed: Oct. 27, 1976

[30] Foreign Application Priority Data

Nov. 6, 1975 [JP] Japan .................. 50/133868

[51] Int. Cl.³ .................. A61K 31/445; C07D 221/26
[52] U.S. Cl. ....................... 424/267; 546/97
[58] Field of Search .............. 260/293.54, DIG. 13; 424/267; 546/97

[56] References Cited

U.S. PATENT DOCUMENTS

| | | | |
|---|---|---|---|
| 3,631,051 | 12/1971 | Atsumi et al. | 260/293.54 |
| 3,632,591 | 1/1972 | Albertson et al. | 260/DIG. 13 |
| 3,833,595 | 9/1974 | Atsumi et al. | 260/293.54 |

FOREIGN PATENT DOCUMENTS 48-16512 5/1973 Japan .................. 260/293.54

OTHER PUBLICATIONS

DeStevens, G. (editor), *Analgetics*, Academic Press, New York, 1965, p. 163.

*Primary Examiner*—John D. Randolph
*Assistant Examiner*—Richard A. Schwartz
*Attorney, Agent, or Firm*—Stevens, Davis, Miller & Mosher

[57] ABSTRACT

2-Substituted-2'-methyl-6,7-benzomorphan derivatives of the formula:

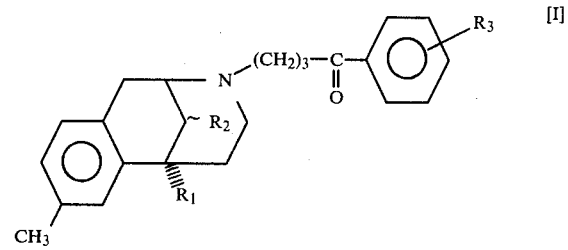

wherein $R_1$ and $R_2$ are each hydrogen or $C_1$–$C_3$ alkyl; and $R_3$ is hydrogen, halogen or $C_1$–$C_3$ alkyl, and pharmaceutically acceptable salts thereof, which are useful as non-addicting analgesics with sedative effects, are prepared by the reaction of a 6,7-benzomorphan derivative of the formula:

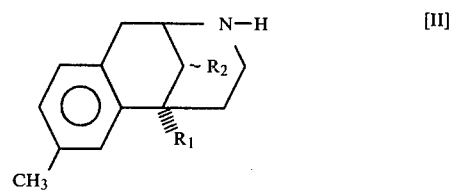

wherein $R_1$ and $R_2$ are as defined above, with a reactive derivative of an alcohol compound of the formula:

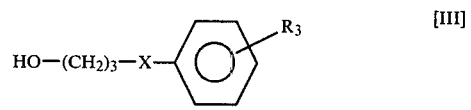

wherein X is an optionally protected carbonyl group; and $R_3$ is as defined above, optionally followed by the elimination of the protective group of the carbonyl group, or by the oxidation of a 6,7-benzomorphan derivative of the formula:

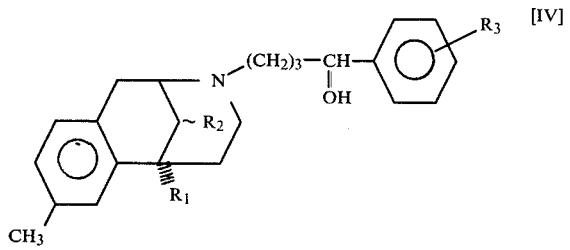

wherein $R_1$, $R_2$ and $R_3$ are as defined above.

10 Claims, No Drawings

ANALGESIC BENZOMORPHAN DERIVATIVES

This invention relates to 2-substituted-2'-methyl-6,7-benzomorphan compounds and pharmaceutically acceptable acid addition salts thereof, which are useful as non-addicting analgesics having a sedative effect, to a preparation of the same and to an analgesic composition containing the same as an active ingredient.

Hitherto, many benzomorphan series compounds (e.g. Phenazocine, Pentazocine) have been developed as analgesic drugs, but many of them cause drug addiction and product narcotic symptoms at their usual dosages, and most of them do not produce any appreciable analgesia when they are orally administered. For example, 2'-hydroxy-2,5,9-trimethyl-6,7-benzomorphan as disclosed in U.S. Pat. No. 3,138,603 has an addiction liability, though it produces a potent analgesia, and hence its therapeutical usage is restricted. As disclosed in U.S. Pat. No. 3,833,595, 2-[γ-(p-fluorobenzoyl)-propyl]-2'-hydroxy-5,9-dimethyl-6,7-benzomorphan exhibits a significant analgesic activity without causing drug addiction. However, this compound is effective when administered parenterally rather than orally.

As the result of a study, the compounds of the formula [I] as defined hereinafter and their pharmaceutically acceptable acid addition salts have been found to exhibit a strong analgesic activity without causing drug dependency or drug addiction not only through parenteral administrations but also through an oral administration, and to be useful as a non-addictive analgesic drug. Further, the compounds of the present invention have also been found to possess a sedative activity as well. The compounds of this invention are thus useful as a non-addictive analgesic agent having a sedative effect, which can be administered parenterally as well as orally.

Thus it is an object of the present invention to provide novel 2-substituted-2'-methyl-6,7-benzomorphan derivatives and non-toxic pharmaceutically acceptable acid addition salts thereof. It is another object of the present invention to provide a process for preparing the 2-substituted-2'-methyl-6,7-benzomorphan derivatives. It is a further object of the present invention to provide an analgesic composition comprising the 2-substituted-2'-methyl-6,7-benzomorphan derivative as an active ingredient and a pharmaceutically acceptable carrier or diluent.

The 2-substituted-2'-methyl-6,7-benzomorphan derivatives provided by this invention are of the formula:

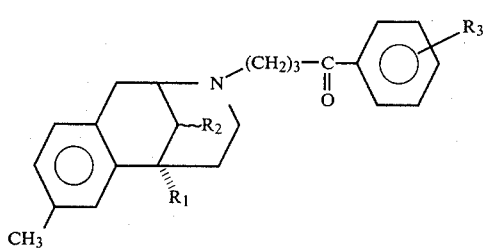

[I]

wherein $R_1$ and $R_2$ are each independently hydrogen or $C_1$-$C_3$ alkyl; and $R_3$ is hydrogen, halogen (preferably, fluoro, chloro or bromo) or $C_1$-$C_3$ alkyl; and non-toxic pharmaceutically acceptable acid addition salts thereof.

In view of the pharmacological properties mentioned above, a preferred class of compounds are the 2-substituted-2'-methyl-6,7-benzomorphan derivatives of the formula [I], wherein $R_1$ and $R_2$ are independently $C_1$-$C_3$ alkyl and $R_3$ is hydrogen, halogen or $C_1$-$C_3$ alkyl. A particularly preferred class of compounds are the 2-substituted-2'-methyl-6,7-benzomorphan derivatives of the formula [I], wherein $R_1$ and $R_2$ are independently $C_1$-$C_3$ alkyl and $R_3$ is halogen (preferably fluoro).

The compounds of the formula [I] of this invention can be prepared by reacting 6,7-benzomorphan derivatives of the formula:

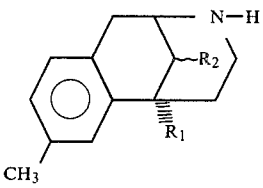

[II]

wherein $R_1$ and $R_2$ are as defined above, with reactive derivatives of alcohol compounds of the formula:

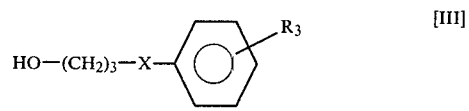

[III]

wherein $R_3$ is as defined above and X is an optionally protected carbonyl group, and subsequently eliminating, if any, the protective group of the carbonyl group.

Referring more particularly to the above process, the reaction is usually carried out in an inert solvent, preferably inert organic solvent (e.g. n-hexane, benzene, toluene, xylene, chloroform, dimethylformamide, methanol, ethanol, isopropanol) at a temperature ranging from 20° C. to 200° C., preferably from 50° C. to 150° C. It is preferable to carry out the reaction in the presence of a basic substance such as sodium carbonate, potassium carbonate, sodium bicarbonate, potassium bicarbonate, sodium hydroxide, potassium hydroxide, sodium amide, sodium hydride, pyridine, triethylamine and the like.

The reactive derivatives of the compounds of the formula [III] may be a derivative of the compounds of the formula [III] wherein the hydroxyl group is replaced by an arylsulfonyloxy (e.g. tosyloxy), or alkylsulfonyloxy (e.g. methanesulfonyloxy) group or a halogen atom. The optionally protected carbonyl group represented by the symbol X may be a carbonyl group which is optionally protected in the form of a ketal such as dimethyl ketal, ethylene ketal, 2,2-dimethylpropan ketal, propane ketal or ethylenethioketal. These protective groups can be eliminated after the reaction by, for example, hydrolysis with an acid.

This hydrolytic elimination can be carried out in the presence of a solvent, for example, water, an alcohol such as methanol, ethanol, n- or iso- propanol, n- butanol or the like, preferably at a temperature ranging from room temperature to the boiling point of the solvent used. In this reaction employment of a catalytic amount of acid is necessary, examples of which include mineral acids such as hydrochloric acid, sulfuric acid and phosphoric acid, and acetic acid and the like. The reaction is usually completed after 0.5 to 2 hours.

The reaction product is readily recovered from the reaction mixture by a conventional separation procedure such as filtration or precipitation.

The compounds of the formula [II] as mentioned above have already been known (Canadian Pat. No. 879,692) and they can be prepared by using a conventional process.

An alternative method for preparing the compounds of the formula [I] is oxidation of 6,7-benzomorphan derivatives of the formula:

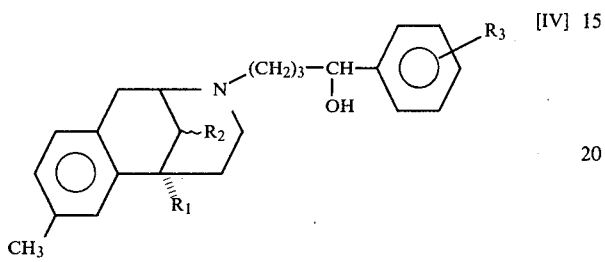

wherein $R_1$, $R_2$ and $R_3$ are as defined above with an oxidizing agent.

Examples of the oxidizing agents to be used in this process include chromium trioxide, manganates and derivatives thereof.

The reaction is preferably carried out in the presence of a solvent. The reaction solvent depends on the oxidizing agent used, and is generally selected from water, acetone, acetic acid, chloroform, carbon tetrachloride, benzene, ethyl acetate, pyridine, dimethylformamide, sulfuric acid and any other solvents which are substantially inert under the conditions of the reaction. The reaction may be carried out at a temperature ranging from $-10°$ C. to $50°$ C., preferably at room temperature.

Jones reagent (which is a mixture of chromic acid, concentrated sulfuric acid and water) is another preferred oxidizing agent for this process and in this case the reaction is normally carried out at a temperature from $-5°$ C. to $30°$ C., preferably from $0°$ C. to $10°$ C.

The compounds of the formula [IV] are novel compounds and are prepared by a process known per se (as disclosed in British Pat. No. 1,311,387) as shown in the following scheme:

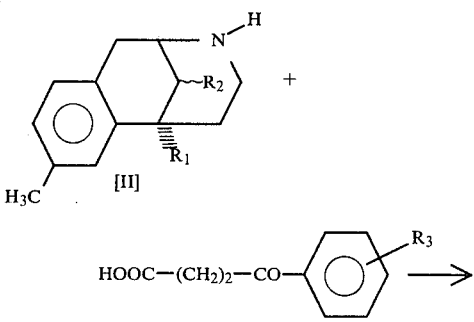

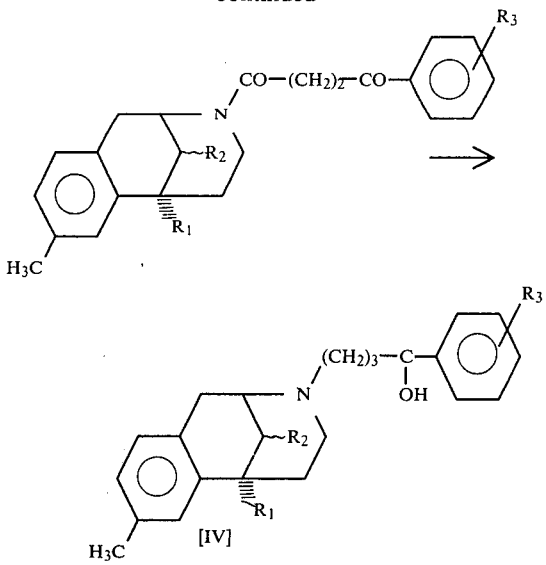

wherein $R_1$, $R_2$ and $R_3$ are as defined above.

When $R_2$ is alkyl, the 2-substituted-2'-methyl-6,7-benzomorphan derivartives of the formula [I] has two stereo isomers, i.e. cis isomer ($R_2$ being $\alpha$-configuration) and trans isomer ($R_2$ being $\beta$-configuration). Each of these isomers can be separated and purified by a conventional procedure such as fractional crystallization, fractional distillation or column chromatography. Alternatively, each of these isomers may be produced from the corresponding cis or trans isomer of the 6,7-benzomorphan derivative of the formula [II] by reacting the same with the reactive derivative of an alcohol of the formula [III]. Still, each of the said isomers has asymmetric carbon atoms, and there can be obtained four optically active isomers (i.e. (+)-cis, (−)-cis, (+)-trans, (−)-trans) by a conventional optical resolution procedure.

The 2-substituted-2'-methyl-6,7-benzomorphan derivative of the formula [I] possesses a basic nitrogen atom in the fundamental structure and hence various acid addition salts can be obtained by the use of organic and inorganic acids such as formic acid, acetic acid, propionic acid, butyric acid, malic acid, fumaric acid, succinic acid, glutamic, acid, tartaric acid, oxalic acid, citric acid, lactic acid, maleic acid, hydroxymaleic acid, glycolic acid, gluconic acid, glucuronic acid, saccharic acid, ascorbic acid, phenylacetic acid, benzoic acid, p-aminobenzoic acid, phthalic acid, salicylic acid, anthranilic acid, p-hydroxybenzoic acid, p-aminosalicyclic acid, picolinic acid, 3-hydroxy-2-naphthoic acid, 3-indoleactic acid, barbituric acid, sulfamic acid, quinic acid, tropic acid, methanesulfonic acid, ethanesulfonic acid, benzenesulfonic acid, p-toluenesulfonic acid, hydroxyethenesulfonic acid, hydrofluoric acid, hydrochloric acid, hydrobromic acid, hydroiodic acid, perchloric acid, nitric acid, sulfuric acid, phosphoric acid and the like. The salt-forming process can be carried out in the manner known per se in the art.

As stated previously, the compounds of the formula [I] of the present invention have a strong analgesic activity. In the writhing test, for instance, 2-[γ-(p-fluorobenzoyl)-propyl]-2',5,9-trimethyl-6,7-benzomorphan was found to be more effective than pentazocine (i.e. 2'-hydroxy-2-(3''-methyl-2''-butenyl)-5,9-dimethyl- 6,7-benzomorphan9, which is one of the most effective commercially available analgesics, in both oral and subcutaneous administractions as shown in Table 1.

TABLE 1

| Compound | ED$_{50}$ (mg/kg) | |
| --- | --- | --- |
| | SC | PO |
| 2-[γ-(p-Fluorobenzoyl)-propyl]-2',5,9-trimethyl-6,7-benzomorphan hydrobromide | 7.9 | 9.6 |
| Pentazocine(2'-hydroxy-5,9-dimethyl-2-(3''-methyl-2''-butenyl)-6,7-benzomorphan).lactate | 17.6 | 98 |
| Morphine . hydrochloride | 1.6 | 7.0 |

Note:
The test was based on the specific antagonism of the test compound to typical syndrome produced by intraperitoneal injection of 0.6% aqueous acetic acid. The syndrome was characterized by intermittent contractions of the abdomen, twisting and turning of the trunk and extension of the hind legs. A group of 5 mice was used for each dose level. The test compound was administered 60 minutes before the injection of acetic acid subcutaneously (sc) or orally (po). The number of mice which showed no pain response was recorded. The ED$_{50}$ value was calculated according to the Litchfield-Wilcoxen's method.

In the abstinence syndrome test, no drug depencency was observed in animals that received subcutaneously or orally the compounds of the formula [I] of the present invention for over one month. For example, 2-[γ-(p-fluorobenzoyl)-propyl]-2',5,9-trimethyl-6,7-benzomorphan did not exhibit any addictive property, unlike morphine or 2'-hydroxy-2,5,9-trimethyl-6,7-benzomorphan (U.S. Pat. No. 3,138,603), as shown in Table 2.

TABLE 2

| Compound | Dose (mg/kg/day for 4 weeks) | Abstinence syndrome |
| --- | --- | --- |
| 2-[γ-(p-Fluorobenzoyl)-propyl]-2',5,9-trimethyl-6,7-benzomorphan hydrobromide | 40 | − |
| Morphine . hydrochloride | 20 | +++ |
| 2'-Hydroxy-2,5,9-trimethyl-6,7-benzomorphan | 20 | ++ |

Note:
Groups of male rats of Wister strain (body weight, 150 g), each group consisting of 20 male rats, were subcutaneously given the test compound twice a day for 4 consecutive weeks. On the next day after drug withdrawal, body weight was measured. The symbols have the following meanings: +++, severe decrease (about 5% decrease); ++, moderate decrease; +, mild decrease; −, no decrease. A marked decrease is taken as an indication of the possession of a narcotic property by the test compound.

Unlike morphine or other known benzomorphan compounds, the compounds of the formula [I] of this invention do not exhibit any serious side effects such as nausea, vomiting, respiratory depression and the like at their usual dosage and hence they can be more safely administered compared with these known analgesics.

The compounds of the formula [I] of the present invention may be administered orally, parenterally (i.e. intramuscularly, intravenously, subcutaneously) or rectally in the form of solid or liquid preparations in order to relieve a patient (i.e. animals including human beings, cattle and poultry) from pain caused by, for example, injury, painful diseases (e.g. terminal cancer), operations and the like. For example, they may be administered orally alone or in the form of tablets, capsules, or powders, which may contain conventional adjuvants such as calcium stearate, starch, lactose, talc, magnesium stearate, gum acacia and the like, or they may be injected parenterally in the form of sterile solutions which contain other solutes, for example, saline or glucose. Compositions for rectal administration may take the form of suppositories and the carrier comprises a conventional suppository base such as polyethylene glycol, lanolin or coconut butter. These preparations can be prepared by the procedures known per se in the art.

Dosage of the compounds of this invention will vary with the form of administration, the reaction, body weight and conditions of a patient, the particular compound chosen, degree of pain and other factors and the particular dosage of the compounds of the present invention will be determined by physicians taking these factors into consideration, as in the case of the known analgesics. In general, usual doses of the present compounds of the formula [I] are 0.015 to 2.0 mg/kg, preferably 0.1 to 1.0 mg/kg orally or parenterally, 1 to 6 times a day.

Practical and presently preferred embodiments of the present invention are shown in the following Examples. Modifications of the procedures shown in these Examples will be obvious to those skilled in the art, and these Examples do not limit the scope of the invention.

EXAMPLE 1

2-[γ-(p-Fluorobenzoyl)-propyl]-2',5,9-trimethyl-6,7-benzomorphan

To a mixture of 2.0 g of 2',5,9-trimethyl-6,7-benzomorphan oxalate, 1.6 of sodium bicarbonate and 20 ml of dimethylformamide is added 2.4 g of 4-(p-fluorophenyl)-4,4-ethylenedioxy-1-chlorobutane. The resultant mixture is stirred at 130° C.–145° C. for 4 hours. The solvent is removed under reduced pressure and to the residue are added 40 ml of methanol, 20 ml of water and 3 ml of concentrated hydrochloric acid. The mixture is refluxed for 1 hour. After the reaction mixture is concentrated under reduced pressure, the mixture is made alkaline with excess aqueous ammonia, and is extracted with chloroform. The chloroform extracts are washed with water saturated with sodium chloride, dried over anhydrous sodium sulfate, and filtered. The filtrate is concentrated to give 2-[γ-(p-fluorobenzoyl)-propyl]-2',5,9-trimethyl-6,7-benzomorphan as a viscous oil.

This 6,7-benzomorphan is dissolved in ether and gaseous hydrogen bromide is introduced to the solution. Ths solvent is removed, and the residue is recrystallized from isopropyl alcohol. This hydrobromide has a melting point of 206.5° C. to 207.5° C.

IR$\nu_{paraffin}^{cm-1}$: 2650, 2580, 1690, 1600, 1500.

EXAMPLE 2

2-(γ-Benzoyl-propyl)-2',5,9-trimethyl-6,7-benzomorphan

According to the procedure of Example 1, the reaction of 2.0 g of 2',5,9-trimethyl-6,7-benzomorphan oxalate with 2.0 g of 4-phenyl-4,4-ethylenedioxy-1-chlorobutane gives 2-(γ-benzoyl-propyl)-2',5,9-trimethyl-6,7-benzomorphan hydrobromide, m.p. 198.5°–200.5° C.

IR$\nu_{paraffin}^{cm-1}$: 2625, 2570, 1690, 1590, 1580.

EXAMPLE 3

5-Ethyl-2-[γ-(p-fluorobenzoyl)-propyl]-2',9-dimethyl-6,7-benzomorphan

According to the procedure of Example 1, the reaction of 1.5 g of 5-ethyl-2',9-dimethyl-6,7-benzomorphan oxalate with 1.7 g of 4-(p-fluorophenyl)-4,4-ethylenedioxy-1-chlorobutane gives 5-ethyl-2-[γ-(p-fluorobenzoyl)-propyl]-2',9-dimethyl-6,7-benzomorphan hydrobromide, m.p. 184°–185° C.

IR$\nu_{paraffin}^{cm-1}$: 2700, 2570, 1690, 1600, 1230.

EXAMPLE 4

2',5,9-Trimethyl-2-[γ-(p-methylbenzoyl)-propyl]-6,7-benzomorphan

A mixture of 0.31 g of 2',5,9-trimethyl-6,7-benzomorphan oxalate, 0.16 g of sodium carbonate, 0.36 g of 1-chloro-4-(p-methylphenyl)-4,4-ethylenedioxy-butane and 10 ml of dimethylformamide is refluxed with stirring for 2 hours. The precipitate produced is filtered off and the filtrate is evaporated. To the residual oil, is added a mixture of 6 ml of methanol, 3 ml of water and 0.5 ml of concentrated hydrochloric acid, and the resultant solution is refluxed for 30 minutes. The reaction mixture is evaporated to remove methanol, made basic with excess aqueous ammonia, and extracted with toluene. The extracts are washed, dried and evaporated to give 2',5,9-trimethyl-2-[γ-(p-methylbenzoyl)-propyl]-6,7-benzomorphan as oily residue. This free base is treated with oxalic acid in acetone to give a crystalline solid, m.p. 186.5°–189° C. (dec.).

EXAMPLE 5

2-[γ-(p-Fluorobenzoyl)-propyl]-2',5,9-trimethyl-6,7-benzomorphan (a)

2-(β-p-Fluorobenzoylpropionyl)-2',5,9-trimethyl-6,7-benzomorphan

To a solution of 1.96 g of β-p-fluorobenzoylpropionic acid and 1.01 g of triethylamine in 50 ml of chloroform, is gradually added 1.09 g of ethyl chloroformate while being cooled below 0° C. After being stirred for 30 minutes at a temperature below 0° C. the mixture is added with 1.09 g of 2',5,9-trimethyl-6,7-benzomorphan and stirred at 0°–5° C. for one hour. After being stirred at room temperature overnight, to the reaction mixture is added 200 ml of chloroform. The resultant mixture is washed with 10% $H_2SO_4$, water, 5% $NaHCO_3$ and water, dried over anhydrous sodium sulfate and filtered. The filtrate is concentrated to dryness to give 2-(β-p-fluorobenzoylpropionyl)-2',5,9-trimethyl-6,7-benzomorphan.

(b)

2-(4''-p-Fluorophenyl-4''-hydroxy-1''-butyl)-2',5,9-trimethyl-6,7-benzomorphan Two grams of lithium aluminum hydride is suspended in 50 ml of tetrahydrofuran and to this suspension is gradually added dropwise a solution of 6.6 g of 2-(β-p-fluorobenzoylpropionyl)-2',5,9-trimethyl-6,7-benzomorphan in 20 ml of tetrahydrofuran below 30° C. The mixture is heated under reflux for 6 hours while being continually stirred.

To the reaction mixture cooled in ice, is gradually added 50 ml of tetrahydrofuran and 50 ml of water and the precipitate is filtered off. The filtrate is concentrated to remove the tetrahydrofuran, and extracted with ether. The extract is washed with water and dried over anhydrous sodium sulfate, and then filtered. The solvent is removed to give 2-(4''-p-fluorophenyl-4''-hydroxy-1''-butyl)-2',5,9-trimethyl-6,7-benzomorphan, m.p. 106.5°–108.5° C.

IR$\nu_{paraffin}^{cm-1}$: 1600, 1500, 1211, 840.

(c)

2-[γ-(p-Fluorobenzoyl)-propyl]-2',5,9-trimethyl-6,7-benzomorphan

A cold solution of 26.7 g of chromic acid in 23 ml of concentrated sulfuric acid and 40 ml of water is made up to 100 ml. This solution (Jones reagent) is 8 N with respect to oxygen. 2-(4''-p-Fluorophenyl-4''-hydroxy-1''-butyl)-2',5,9-trimethyl-6,7-benzomorphan (0.5 g) is dissolved in 20 ml of pure acetone (distilled over potassium permanganate), and the reagent described above is added dropwise from a microburette until a persistent orange-brown coloration indicating that oxidation is complete while being continually stirred below 5° C.

After 10 minutes, the resultant mixture is poured into ice-water with stirring and then the solution is made alkaline with aqueous ammonia. The alkaline solution is extracted with ether. The extract is washed with water saturated with sodium chloride, dried over anhydrous sodium sulfate and concentrated to dryness to give a crude product. This 6,7-benzomorphan is dissolved in ether and gaseous hydrogen bromide is introduced to the solution. The solvent is removed and the residue is recrystallized from isopropyl alcohol. From the data of melting point and IR spectra this compound is identified as the same one as given in Example 1.

What is claimed is:

1. A benzomorphan derivative of the formula:

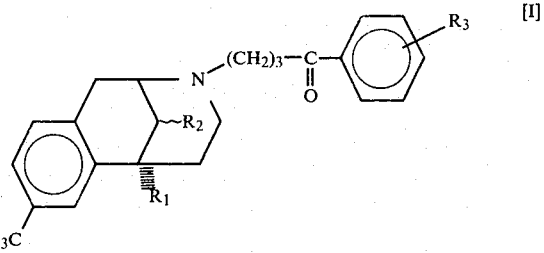

wherein $R_1$ and $R_2$ are each independently hydrogen or $C_1$–$C_3$ alkyl; and $R_3$ is hydrogen, halogen or $C_1$–$C_3$ alkyl, or its non-toxic, pharmaceutically acceptable acid addition salt.

2. A benzomorphan derivative according to claim 1, wherein $R_1$ and $R_2$ are each independently $C_1$–$C_3$ alkyl.

3. A benzomorphan derivative according to claim 1, wherein $R_1$ and $R_2$ are each independently $C_1$–$C_3$ alkyl and $R_3$ is halogen.

4. A benzomorphan derivative according to claim 1, which is 2-[γ-(p-fluorobenzoyl)-propyl]-2',5,9-trimethyl-6,7-benzomorphan, or its non-toxic, pharmaceutically acceptable acid addition salt.

5. A benzomorphan derivative according to claim 1, which is 2-(γ-benzoyl-propyl)-2',5,9-trimethyl-6,7-benzomorphan, or its non-toxic, pharmaceutically acceptable acid addition salt.

6. A benzomorphan derivative according to claim 1, which is 5-ethyl-2-[γ-(p-fluorobenzoyl)-propyl]-2',9-dimethyl-6,7-benzomorphan, or its non-toxic, pharmaceutically acceptable acid addition salt.

7. A benzomorphan derivative according to claim 1, which is 2-[γ-(p-fluorobenzoyl)-propyl]-2',5-dimethyl-6,7-benzomorphan, or its non-toxic, pharmaceutically acceptable acid addition salt.

8. A benzomorphan derivative according to claim 1, which is 2',5,9-trimethyl-2-[γ-(p-methylbenzoyl)-propyl]-6,7-benzomorphan, or its non-toxic, pharmaceutically acceptable salt.

9. An analgesic composition comprising an analgesically effective amount of a benzomorphan derivative as claimed in claim 1 and a pharmaceutically acceptable carrier or diluent.

10. A method for relieving a patient from pain which comprises administering an analgesically effective amount of a benzomorphan derivative as claimed in claim 1 alone or in combination with a pharmaceutically acceptable carrier or diluent.

* * * * *